(12) United States Patent
Gautier et al.

(10) Patent No.: US 7,799,799 B2
(45) Date of Patent: Sep. 21, 2010

(54) INDOLIZINE DERIVATIVES, METHOD FOR PREPARING SAME, AND THERAPEUTIC COMPOSITIONS COMPRISING SAME

(75) Inventors: Patrick Gautier, Antony (FR); David Marchionni, Antony (FR); Alain Roccon, Antony (FR); Bernard Tonnerre, Antony (FR); Jean Wagnon, Antony (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/116,996

(22) Filed: May 8, 2008

(65) Prior Publication Data

US 2008/0287485 A1 Nov. 20, 2008

Related U.S. Application Data

(63) Continuation of application No. PCT/FR2006/002551, filed on Nov. 21, 2006.

(30) Foreign Application Priority Data

Nov. 23, 2005 (FR) .................................. 05 11849

(51) Int. Cl.
*A61K 31/437* (2006.01)
(52) U.S. Cl. ........................ 514/299; 546/112; 548/516

(58) Field of Classification Search ............... 514/299; 546/112; 548/516
See application file for complete search history.

(56) References Cited

U.S. PATENT DOCUMENTS 4,103,012 A 7/1978 Gubin et al.
5,223,510 A 6/1993 Gubin et al.

FOREIGN PATENT DOCUMENTS

WO WO2007060318 A1 5/2007

*Primary Examiner*—Janet L Andres
*Assistant Examiner*—David E Gallis
(74) *Attorney, Agent, or Firm*—Ronald G. Ort

(57) ABSTRACT

The present invention is directed to compounds of formula (I):

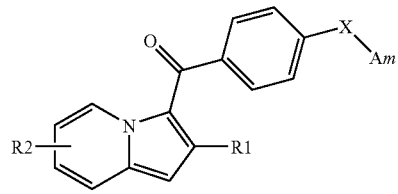

described as novel indolizine derivatives and to a method for their preparation along with pharmaceutical compositions thereof whose substituents are as described in the specification.

15 Claims, No Drawings

INDOLIZINE DERIVATIVES, METHOD FOR PREPARING SAME, AND THERAPEUTIC COMPOSITIONS COMPRISING SAME

FIELD OF THE INVENTION

The present invention relates to novel indolizine derivatives, to a method for their preparation and to pharmaceutical compositions containing them.

BACKGROUND OF THE INVENTION

French patent FR-A-2 341 578 and European patent EP-A-0 471 609 describe indolizine derivatives which have remarkable pharmacological properties, especially antiarrhythmic properties, since those derivatives have been shown to be capable of suppressing or staving off ventricular and auricular rhythm problems. The majority of the compounds described have electrophysiological properties in classes 1, 2, 3 and 4 of the Vaughan-Williams classification which in addition to their antiarrhythmic properties, indicate their bradycardiac, anti-hypertensive and α and β non-competitive anti-adrenergic properties. Such properties render the compounds in question very useful in the treatment of certain pathological syndromes of the cardiovascular system, in particular in the treatment of angina pectoris, hypertension or ventricular or supraventricular arrhythmia. Similarly, such compounds are used to treat cardiac insufficiency, myocardial infarction complicated or otherwise by cardiac insufficiency, or to prevent post-infarction mortality.

However, such compounds have the disadvantage of being insoluble or only slightly soluble in water, in particular at pH=4 and especially at a physiological pH.

Amiodarone, which is an auricular and ventricular antiarrhythmic which is administered orally and intravenously, is a molecule which is insoluble in water; the injectable solution thus contains solvents such as polysorbate 80 and benzyl alcohol. Such solvents induce hypotensive and negative inotropic effects in patients. The injectable solution also causes local venous intolerances which are prevented by recommending a central injection in a specialized hospital environment.

Dronedarone, a derivative of benzofuran, contains no iodine in its chemical structure, in contrast to amiodarone, and is also an auricular and ventricular antiarrhythmic which is administered orally and intravenously. Its low solubility (solubility in water S=0.247 mg/ml at a pH of 3) limits the possibility of preparing and storing it in the form of an injectable substance.

That low solubility substantially limits the possibility of preparing and storing them in the form of an injectable substance.

In the context of the invention, novel indolizine derivatives have now been discovered which have good solubility in water while retaining or even improving their pharmacological properties, especially their antiarrhythmic properties. Their good solubility in water, in particular at pH=4, allows injectable pharmaceutical forms to be produced.

The compounds of the present invention are molecules which are soluble in water which can be administered intravenously in a physiological solution (0.9% sodium chloride) or glucosated, and which have the electrophysiological, haemodynamic and antiarrhythmic properties of amiodarone.

Furthermore, these novel compounds also exhibit good metabolic stability.

Thus, the invention proposes indolizine derivatives comprising an aminoalkylbenzoyl chain represented by formula (I) below.

Thus, the present invention concerns novel indolizine derivatives with general formula (I):

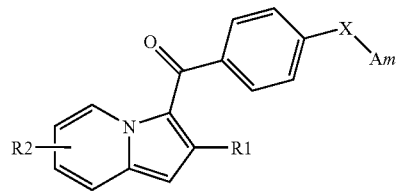

in which:

X represents a —$(CH_2)_n$— radical where n is a whole number from 1 to 6, or a group with formula $CH_2$—Z—$(CH_2)_2$—, in which Z represents an $O(CH_2)_m$— group in which m is a whole number from 0 to 3; $R_1$ represents a linear, branched or cyclic $C_1$-$C_8$ alkyl radical; Am represents an $NR_3R_4$ group in which $R_3$ and $R_4$ are identical or different and independently of each other represent:

a hydrogen atom;

a linear, branched or cyclic $C_1$-$C_6$ alkyl radical or a $C_1$-$C_3$ radical substituted with a $C_3$-$C_6$ cycloalkyl radical;

or a $(CH_2)_l$—O—B radical in which B represents a hydrogen atom or a —$(CH_2)_k$H alkyl radical, where l and k are whole numbers, $l \geq 2$ and $l+k \leq 6$;

or $R_3$ and $R_4$ together with the nitrogen atom to which they are attached form a heterocycle containing 4 to 6 links which may optionally contain one or more heteroatoms selected from N and O and optionally carrying one or more substituents selected from a linear, branched or cyclic $C_1$-$C_6$ alkyl radical;

$R_2$ represents a hydrogen atom or a linear, branched or cyclic $C_1$-$C_6$ alkyl radical;

and their pharmaceutically acceptable salts.

In a first variation, the invention concerns indolizine derivatives as defined above in which X represents a —$(CH_2)_n$— radical where n is a whole number from 1 to 6.

In a second variation, the invention concerns indolizine derivatives as defined above in which X represents a group with formula $CH_2$—Z—$(CH_2)_2$—, in which Z represents an $O(CH_2)_m$— group in which m is a whole number from 0 to 3.

More particularly, the invention concerns indolizine derivatives as defined above, characterized in that X represents a $(CH_2)_n$— radical where n is a whole number from 3 to 4.

More particularly, the indolizine derivatives of the invention are characterized in that $R_1$ represents a $C_1$-$C_4$ alkyl radical.

More particularly, the indolizine derivatives of the invention are characterized in that $R_3$ and $R_4$ independently of each other represent a linear $C_1$-$C_4$ alkyl radical.

In particular, the indolizine derivatives of the invention are characterized in that $R_3$ and $R_4$ together form a piperidinyl or piperazinyl group optionally carrying one or more methyl radicals.

In particular, the indolizine derivatives of the invention are characterized in that $R_2$ represents a hydrogen atom.

The compounds of formula (I) can exist in the form of bases or in the form salified with acids or bases, in particular pharmaceutically acceptable acids or bases. Such addition salts form part of the invention.

These salts are advantageously prepared with pharmaceutically acceptable acids, but the salts of other acids that are of use, for example, for the The compounds of formula (I) can also exist in the form of hydrates or of solvates, i.e. in the form of associations or of combinations with one or more molecules of water or with a solvent. Such hydrates and solvates also form part of the invention.

The invention also pertains to pharmaceutically acceptable salts of compounds with formula (I) formed from an organic or inorganic acid.

Examples of organic salts of this type which may be cited are the malonate, dodecanoate, oxalate, maleate, fumarate, methanesulphonate, benzoate, ascorbate, pamoate, succinate, hexamate, bis-methylenesalicylate, ethanedisulphonate, acetate, propionate, tartrate, salicylate, citrate, gluconate, lactate, malate, cinnamate, mandelate, citraconate, aspartate, palmitate, stearate, itaconate, glycolate, p-aminobenzoate, glutamate, benzenesulphonate, p-toluenesulphonate and theophylline acetate, as well as the salts formed from an amino acid, such as the lysine or histidine salt.

Inorganic salts of this type which may be cited are hydrochlorides, hydrobromides, sulphates, sulphamates, phosphates and nitrates.

More particularly, the invention concerns indolizine derivatives as defined above, characterized in that the pharmaceutically acceptable salt is selected from the oxalate and the hydrochloride.

The invention also pertains to the preparation of compounds with formula (I).

Thus, the present invention concerns a method for preparing derivatives with formula (I) as defined above, comprising the reaction of an amine H—Am with a compound represented by formula (II):

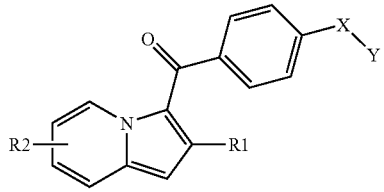

II in which Y represents a halogen atom and the other substituents are as defined above.

The invention also concerns a method comprising a method for preparing a compound with formula (II) as defined above and comprising the reaction of a compound represented by formula (III):

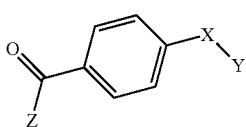

III with a compound represented by formula (IV):

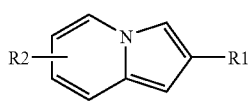

IV

Thus, in accordance with the invention, compounds with formula (I) in which X represents a —$(CH_2)_n$— radical as defined above are prepared in accordance with the following reaction scheme:

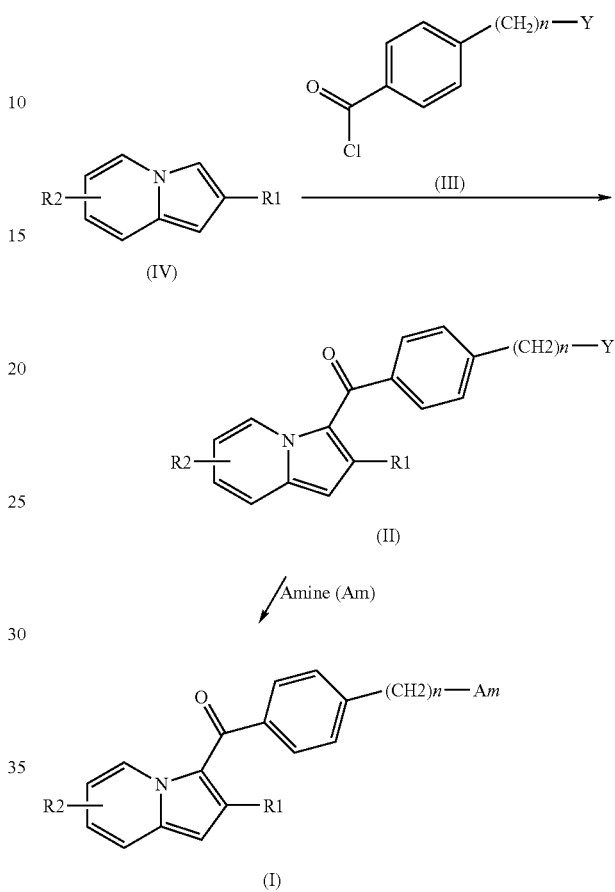

in which Y represents a halogen, for example Cl or Br, and n and the $R_1$, $R_2$, Am groups have the same meanings as given above.

Reference may be made to U.S. Pat. No. 6,949,583 for the preparation of the compounds with formula (III).

To prepare compounds with formula (IV), reference may be made to the publication EUR J. MED. CHEM-CHEMICAL THERAPEUTICA, NOVEMBER-DECEMBER 1975-10, No 6, pp 579 to 584 and to LABAZ's U.S. Pat. No. 4,103,012.

Similarly, to prepare indolizine derivatives with formula (I) by condensing a secondary amine with formula H—Am with the chlorinated derivative with formula (II) and to prepare compounds with formula (II) by reacting compounds with formula (III) with derivatives with formula (IV), reference should be made to the document U.S. Pat. No. 4,103,012.

In accordance with the invention, to prepare compounds with formula (I) when X represents a group with formula $CH_2$—Z—$(CH_2)_2$—, in which Z represents an $O(CH_2)_m$— group as defined above, reference should be made to U.S. Pat. No. 6,949,583 and to Monatsh Chem: 129; 3; 1998; 309-318 and to the following reaction scheme:

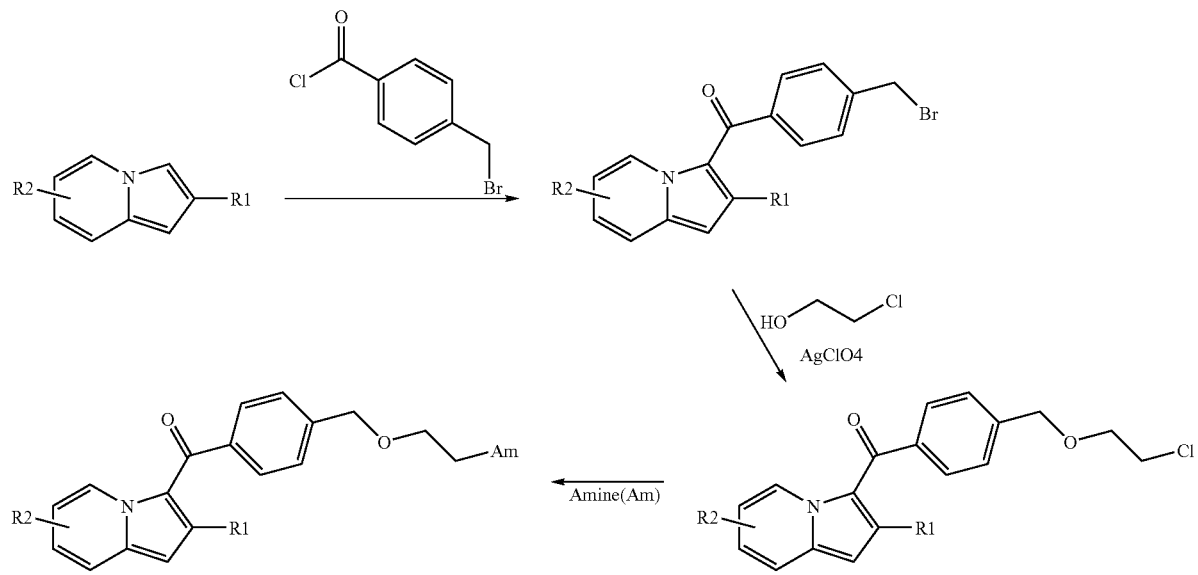

in which the groups $R_1$, $R_2$, Am have the same meanings as given above.

The invention also pertains to a pharmaceutical or veterinary composition, characterized in that it contains, as the active principle, at least one indolizine derivative with formula (I) as defined above or a pharmaceutically acceptable salt thereof, in association with a pharmaceutically acceptable vehicle or an appropriate excipient.

As an example, the pharmaceutical compositions of the present invention may be formulated for oral, sublingual, subcutaneous, intramuscular, intravenous, transdermal or rectal administration. Preferably, the compositions are present in an injectable form, exploiting the good solubility characteristics of the derivatives of the invention.

Regarding the administration unit, this may take the shape, for example, of a tablet, a dragée, a capsule, a gellule, a powder, a suspension, a syrup or granules for oral administration, a suppository for rectal administration or a solution or suspension for parenteral administration.

The pharmaceutical compositions of the invention may, for example, comprise, per administration unit, 50 to 500 mg by weight of active ingredient for oral administration, 50 to 200 mg of active ingredient for rectal administration and 50 to 150 mg of active ingredient for parenteral administration.

Depending on the administration route selected, the pharmaceutical or veterinary compositions of the invention are prepared by associating at least one of the compounds with formula (I) or a pharmaceutically acceptable salt of that compound with a suitable excipient, the latter possibly being constituted, for example, by at least one ingredient selected from the following substances: lactose, starches, talc, magnesium stearate, polyvinyl pyrrolidone, alginic acid, colloidal silica, distilled water, benzyl alcohol or sweetening agents.

When they are in tablet form, they may be treated so that they have an extended or delayed action and so that they continuously release a predetermined quantity of active principle.

The invention also concerns indolizine derivatives with general formula (I) as defined above for their use as a drug.

The present invention thus concerns drugs comprising indolizine derivatives with general formula (I) as defined above.

The indolizine derivatives with general formula (I) of the present invention as defined above may be used to prepare a drug for the treatment of pathological syndromes of the cardiovascular system. More particularly, the indolizine derivatives with general formula (I) of the present invention as defined above may be used to prepare a drug for the treatment of angina pectoris, hypertension, ventricular arrhythmia, supraventricular arrhythmia, in particular auricular fibrillation, cardiac insufficiency, myocardial infarction which may or may not be complicated by cardiac insufficiency or for the prevention of post-infarction mortality.

The results of pharmacological tests carried out to determine the properties of the compounds of the invention as regards the cardiovascular system are recorded below.

I. Ventricular Arrhythmias

This test aims to determine the capacity of the compounds of the invention to protect against arrhythmias caused by re-perfusion of a previously ischaemiated coronary artery. To this end, we used the method set out by MANNING A. S. et al. in Circ. Res. 1984, 55: 545-548 modified as follows:

Firstly, rats sorted into batches were anaesthetized with sodium pentobarbital (60 mg/kg intraperitoneally) then they were intubated to assist respiration.

A cannula was then placed in a jugular vein for intravenous administration, a catheter was placed in a carotid artery to measure the arterial pressure, and cutaneous electrodes were placed to measure the ECG. After equilibrating the parameters, an intravenous dose of the compound to be studied was administered and 5 minutes later, after carrying out a thoracotomy, a loop of ligature was placed around the left anterior descending coronary artery in the immediate proximity of its origin. Thus, that artery was occluded for 5 minutes by tension on the ends of the ligature. Re-perfusion was obtained by releasing the tension.

The arrhythmias induced by that re-perfusion were then evaluated.

An analogous test was carried out after oral administration of the compound. In this case, the study compound was administered 60 to 120 minutes before ligating the left anterior descending coronary artery.

The results of these tests showed that the compounds of the invention, administered in doses in the range 0.3 to 10 mg/kg intravenously and 30 to 100 mg/kg orally, significantly or completely protected the treated animals from ventricular arrhythmia.

II. Antiadrenergic Properties

This test aims to determine the capacity of the compounds of the invention to reduce the increase in blood pressure induced by phenylephrin (anti-α effect) and the acceleration in cardiac frequency induced by isoprenaline (anti-β effect) in a dog which had been anaesthetized beforehand with pentobarbital and chloralose.

Initially, for each dog the dose of phenylephrin (5 μg/kg was determined which provoked an increase in the arterial pressure in the range 25 to 40 mmHg and the dose of isoprenaline (0.5 or 1 μg/kg) which should cause an increase in cardiac frequency in the range 40 to 110 beats/minute.

Every 10 minutes, the doses of phenylephrin and isoprenaline determined in this way were injected alternately and after obtaining two successive reference responses, a dose of the compound to be studied was administered intravenously.

Anti-α Effect

The percentage reduction by the compound of the invention in the hypertension caused compared with the reference hypertension obtained before injecting that compound was recorded.

Anti-β Effect

The percentage reduction in the study compound of the acceleration caused in the cardiac frequency was recorded.

The results of these tests showed that in doses of 3 to 10 mg/kg, the compounds of the invention exhibited anti-α and/or anti-β effects, resulting in reductions in the provoked hypertension and/or the provoked increase in cardiac frequency, of up to 50%.

III. Auricular Arrhythmias

This test aims to evaluate the efficacy of the compounds of the invention as regards auricular arrhythmia (left auricular vulnerability) induced by extra stimuli in the anaesthetized pig using the method described in Naunyn-Schmiedeberg's Arch Pharmacol 2001, 363: 166-174.

The study compounds were administered in a dose of 3 mg/kg in slow 5-minute intravenous perfusions. The haemodynamic and electrocardiographic parameters and the right and left auricular refractory periods were determined before and after administering the study compound.

In a dose of 3 mg/kg, the compounds of the invention generally abolished 100% of non-sustained fibrillation or auricular flutter episodes induced by early extra stimuli. In this dose, significant increases in the effective auricular refractory periods were observed for different basal values of the cardiac period.

IV. Effects of Cardiac Ion Channels

This test aims to determine the effects of the compounds of the invention on cardiac ion channels.

The compounds of the invention (1 to 5 μM) inhibited the permeability of human hERG ($IK_r$) and hKv1.5 ($IK_{ur}$) gene channels expressed in the CHO (Chinese hamster ovary) cell line. They also inhibited native sodium (Ina), calcium ($ICa_L$) and potassium channel currents, acetylcholine ($IK_{(Ach)}$)-activated and ATP-dependent ($IK_{ATP}$), in guinea pig cardiomyocytes, and potassium channels (Ito and Isus) in rat cardiomyocytes.

Thus, the compounds of the invention are inhibitors of multiple cardiac ion channels.

V. Toxicity

The toxicity of the compounds of the invention proved to be compatible with their therapeutic use.

VI. Solubility

The solubility tests for the compounds of the invention were carried out at pH=4 (starting from a phosphate buffer, pH=6, 0.1M) by HPLC (high performance liquid chromatography) using an $H_2O/CH_3CN/CH_3SO_3H$ gradient and compared with a reference sample (a dilute solution of test product which acts as an internal reference).

The results for solubility, S, and pH are shown in the table below and are expressed in mg/ml.

In general, compounds with formula (I) of the present invention have a solubility of 1 mg/ml or more at pH=4; some of them had a solubility of more than 8 mg/ml or even more than 10 mg/ml.

TABLE OF EXAMPLES

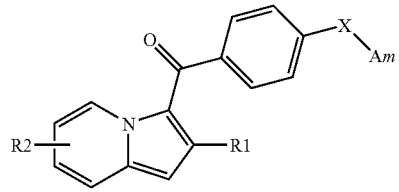

in which $X = (CH_2)_n$

| compound n° | salt | n | $R_1$ | $R_2$ | Am | S/pH |
|---|---|---|---|---|---|---|
| 1 | hydrochloride | 3 | C4H9 | H | | 8.81/5.4 |
| 2 | oxalate | 3 | C2H5 | H | | 7.47/4.07 |
| 3 | hydrochloride | 3 | nC3H7 | H | | >10/5.82 |
| 4 | oxalate | 4 | C4H9 | H | | >10/4.10 |
| 5 | oxalate | 4 | C2H5 | H | | >10/3.96 |
| 6 | hydrochloride | 4 | nC3H7 | H | | >10/5.79 |

-continued

TABLE OF EXAMPLES

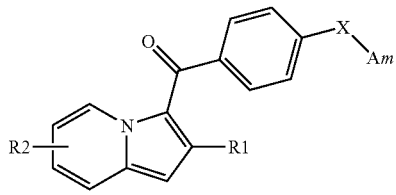

in which $X = (CH_2)_n$

| # | Salt | n | R1 | R2 | Am | Values |
|---|---|---|---|---|---|---|
| 7 | hydrochloride | 3 | C4H9 | H | N(propyl)(propyl) | 8.57/5.65 |
| 8 | hydrochloride | 3 | C2H5 | H | | 8.6/5.82 |
| 9 | hydrochloride | 3 | C3H7 | H | | 5.29/5.82 |
| 10 | hydrochloride | 4 | C4H9 | H | | >10/5.81 |
| 11 | hydrochloride | 4 | C2H5 | H | | >10/5.82 |
| 12 | hydrochloride | 3 | ipr | H | | 1.2/4.3 |
| 13 | hydrochloride | 3 | CH3 | H | | 1.61/7.2 |
| 14 | oxalate | 4 | ipr | H | | 2.33/4.10 |
| 15 | hydrochloride | 4 | CH3 | H | | 1.56/6.33 |
| 16 | hydrochloride | 4 | C3H7 | H | | >10/5.81 |
| 17 | hydrochloride | 3 | C4H9 | H | N(butyl)(propyl) | >10/4.88 |
| 18 | hydrochloride | 3 | C2H5 | H | | 6.51/5.42 |
| 19 | hydrochloride | 3 | C3H7 | H | | 4.07/5.27 |
| 20 | oxalate | 4 | C4H9 | H | | 2.95/4.02 |
| 21 | oxalate | 4 | C2H5 | H | | 6.9/4.08 |
| 22 | oxalate | 4 | C3H7 | H | | 4.08/4.58 |
| 23 | hydrochloride | 3 | C4H9 | H | N(propyl)(ethyl) | >10/6.06 |
| 24 | oxalate | 3 | C2H5 | H | | 5.92/4.51 |
| 25 | hydrochloride | 3 | ipr | H | | 1.71/6.4 |
| 26 | hydrochloride | 3 | CH3 | H | | 1.49/7.14 |
| 27 | oxalate | 4 | ipr | H | N(propyl)(ethyl) | 2.17/6.5 |
| 28 | hydrochloride | 4 | CH3 | H | | 1.54/7.01 |
| 29 | hydrochloride | 3 | C3H7 | H | | >10/5.94 |
| 30 | hydrochloride | 4 | C4H9 | H | | >10/5.85 |
| 31 | oxalate | 4 | C2H5 | H | | >10/4.05 |
| 32 | hydrochloride | 4 | C3H7 | H | | 5.64/5.60 |
| 33 | oxalate | 3 | C4H9 | H | N(butyl)(butyl) | 3.88/5.36 |
| 34 | oxalate | 3 | C4H9 | H | N(butyl)(ethyl) | 5.02/4.14 |
| 35 | oxalate | 3 | C4H9 | H | N(propyl)(CH2-cyclopropyl) | 4.4/4.75 |
| 36 | hydrochloride | 4 | C3H7 | H | NH(propyl) | 2.24/6.3 |
| 37 | hydrochloride | 3 | C4H9 | H | | 1.78/7.14 |
| 38 | hydrochloride | 3 | C4H9 | H | N(methyl)(ethyl) | 1.42/6.7 |

-continued
TABLE OF EXAMPLES
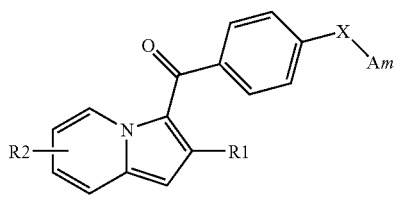
in which X = (CH2)$_n$
| compound n° | salt | n | R$_1$ | R$_2$ | Am | S/pH |
|---|---|---|---|---|---|---|
| 39 | hydrochloride | 3 | C4H9 | H | 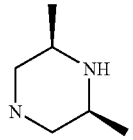 | >10/4.22 |
| 40 | hydrochloride | 3 | C4H9 | H | 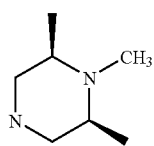 | 9.93/4.3 |
| 41 | oxalate | 3 | C4H9 | H | 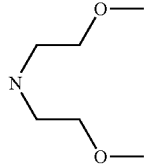 | 7.19/3.95 |
| 42 | oxalate | 3 | C4H9 | H |  | 1.66/5.18 |
| compound n° | salt | n | R$_1$ | R$_2$ in position 6 | Am | S/pH |
|---|---|---|---|---|---|---|
| 43 | hydrochloride | 3 | C4H9 | CH3 | 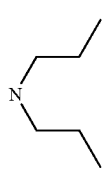 | 4.46/5.65 |
| 44 | hydrochloride | 3 | C4H9 | C2H5 | | >10/6.05 |
| 45 | hydrochloride | 3 | C4H9 | CH3 | 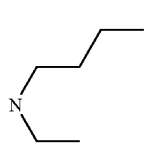 | 5.8/5.95 |
| 46 | hydrochloride | 3 | C4H9 | C2H5 | | 8.92/5.92 |

The following non-limiting examples illustrate the preparation of the compounds and compositions of the invention:

The proton magnetic resonance spectra ($^1$H NMR) described below were recorded at 200 MHz in DMSO-$d_6$ using the DMSO-$d_6$ peak as the reference.

The chemical displacements δ are expressed in parts per million (ppm). The signals observed are expressed as follows: s: singlet; bs: broad singlet; d: doublet; dd: double doublet; t: triplet; dt: double triplet; q: quadruplet; qui: quintuplet; m: mass; mt: multiplet; sxt: sextuplet.

EXAMPLE 1

(2-butyl-6-ethylindolizin-3-yl){4-[3-(dipropylamino)propyl]phenyl}methanone hydrochloride (compound 44)

a) 1-bromohexane-2-one 60 g (0.599 mole) of 2-hexanone was slowly added to a solution of 58.6 g (0.976 mole) of urea in 210 ml of acetic acid at ambient temperature. The medium was cooled to 0° C. in an ice bath then 33 ml of bromine (0.640 mole) was added and it was stirred for 18 hours at ambient temperature. It was poured onto water (1500 ml) and extracted with methylene chloride, the organic phase was washed with a sodium bicarbonate solution, then dried over sodium sulphate and the solution was concentrated.

The residue was distilled under reduced pressure. 76 g of the expected compound was recovered (boiling point: 80-90° C./18 mmHg), contaminated with a little of its isomer, 3-bromohexanone (6%).

b) N-(hexanone-2-yl)-2-methyl-5-ethylpyridinium bromide 21.6 g (0.178 mole) of 5-ethyl-2-methylpyridine was added slowly to 40 g of 1-bromo-2-hexanone (0.223 mole) and stirred for 3 hours at ambient temperature. A viscous medium was obtained which was used as is for the next step.

c) 2-butyl-6-ethyl-indolizine

A solution of 65 g of triethylamine in 370 ml of ethanol was added dropwise to a solution of the product described above in 300 ml of ethanol then it was heated under reflux for 18 hours. It was vacuum concentrated, taken up in ethyl acetate, washed with water then the organic phase was dried over sodium sulphate and concentrated to dryness. Next, it was purified by flash chromatography over silica (eluent: heptane/methylene chloride, 50/50). In this manner, 15 g of the desired compound was obtained in the form of a yellow oil.

Yield: 34%.

d) (2-butyl-6-ethylindolizin-3-yl)[4-(3-chloropropyl)phenyl]methanone

A mixture of 5 g (27 mmoles) of the compound obtained in the preceding step and 5.9 g (27 mmoles) of 4-(3-chloropropyl)benzoyl chloride was heated to 50° C. for 18 hours. It was taken up in water, extracted with dichloromethane, the organic phase was washed with a sodium carbonate solution, then dried over sodium sulphate and concentrated to dryness. It was then purified by flash chromatography over alumina (eluent: heptane/methylene chloride, 50/50). In this manner, 8 g of the desired compound was obtained in the form of an oil.

Yield: 76%.

e) (2-butyl-6-ethylindolizin-3-yl){4-[(3-(dipropylamino)propyl]phenyl}methanone 4 g (10.4 mmoles) of the compound obtained in the preceding step was dissolved in 50 ml of methylisobutyl-ketone in a reactor and 2.7 g (27 mmoles) of dipropylamine and 0.31 g (2 mmoles) sodium iodide were added to this reaction medium and then heated to 110° C. for 48 hours. It was poured into water, extracted with dichloromethane, washed with a sodium bicarbonate solution, dried over sodium sulphate and concentrated to dryness. It was then purified by flash chromatography over alumina (eluent: methylene chloride-ethyl acetate, 80/20). In this manner, 3.9 g of the desired compound was obtained.

Yield: 84%.

f) (2-butyl-6-ethylindolizin-3-yl){4-[3-(dipropylamino)propyl]phenyl}methanone hydrochloride 6.5 ml of a solution of hydrochloric ether (2M in ether) was added to a solution of the product described above (3.9 g) in ether (400 ml), stirred for 30 minutes and the salt which precipitated out was filtered. In this manner, 3.7 g of the desired compound was obtained.

Yield: 88%, MP=140.7° C.

$^1$H NMR spectrum (200 MHz, (DMSO), δ in ppm);

0.65 (t: 3H); 0.79-1.10 (m: 8H); 1.11-1.44 (m: 5H); 1.66 (mt: 4H); 2.03 (mt: 2H); 2.17 (t: 2H); 2.62 (q: 2H); 2.74 (t: 2H); 2.87-3.16 (m: 6H); 6.45 (s: 1H); 7.15 (d: 1H); 7.29-7.65 (m: 5H); 9.36 (s: 1H); 10.49 (bs: 1H)

The following compounds were prepared using the method described above in Example 1, but using appropriate starting substances:

(2-butyl-6-methylindolizin-3-yl){4-[3-(dipropylamino)propyl]phenyl}methanone hydrochloride

MP=140° C.

$^1$H NMR spectrum (200 MHz, (DMSO), δ in ppm); 0.65 (t: 3H); 0.79-1.10 (m: 8H); 1.32 (qui: 2H); 1.66 (m: 4H); 2.03 (mt: 2H); 2.17 (t: 2H); 2.30 (s: 3H); 2.74 (t: 2H); 2.87-3.16 (m: 6H); 6.45 (s: 1H); 7.09 (d: 1H); 7.31-7.61 (m: 5H); 9.34 (s: 1H); 10.60 (bs: 1H)

(2-butyl-6-methylindolizin-3-yl)(4-{3-[ethyl(propyl)amino]propyl}phenyl)methanone hydrochloride

MP=132° C.

$^1$H NMR spectrum (200 MHz, (DMSO), δ in ppm); 0.64 (t: 3H); 0.79-1.09 (m: 5H); 1.09-1.43 (m: 5H); 1.65 (mt: 2H); 2.01 (mt: 2H); 2.15 (t: 2H); 2.29 (s: 3H); 2.74 (t: 2H); 2.85-3.21 (m: 6H); 6.44 (s: 1H); 7.08 (d 1H); 7.25-7.65 (m: 5H); 9.33 (s: 1H); 10.57 (bs: 1H)

(2-butyl-6-ethylindolizin-3-yl)(4-{3-[ethyl(propyl)amino]propyl}phenyl)methanone hydrochloride

MP=148.7° C.

$^1$H NMR spectrum (200 MHz, (DMSO), δ in ppm); 0.64 (t: 3H); 0.79-1.10 (m: 5H); 1.10-1.44 (m: 8H); 1.65 (mt: 2H); 2.01 (mt: 2H); 2.17 (t: 2H); 2.62 (q: 2H); 2.75 (t: 2H); 2.85-3.23 (m: 6H); 6.45 (s: 1H); 7.15 (d 1H); 7.29-7.65 (m: 5H); 9.36 (s: 1H); 10.53 (bs: 1H)

EXAMPLE 2

(2-ethylindolizin-3-yl){4-[3-(diethylamino)propyl]phenyl}methanone oxalate (compound 2)

a) (2-ethylindolizin-3-yl)[4-(3-chloropropyl)phenyl]methanone

A mixture of 8 g (55 mmoles) of 2-ethyl-indolizine and 13.1 g (60 mmoles) of 4-(3-chloropropyl)benzoyl chloride was heated to 50° C. for 18 hours. It was taken up in water, extracted with dichloromethane, washed with a sodium carbonate solution; the organic phase was then dried over sodium sulphate and concentrated to dryness. It was purified by flash chromatography over alumina (eluent: cyclohexane/methylene chloride, 50/50). In this manner, 17 g of the desired compound was obtained in the form of an oil. Yield: 94%.

b) (2-ethylindolizin-3-yl){4-[3-(diethylamino)propyl]phenyl}methanone 4 g (12 mmoles) of the compound obtained in the preceding step was dissolved in 50 ml of methyl isobutylketone in a reactor then 2.3 g (31 mmoles) of diethylamine and 0.36 g (2.4 mmoles) of sodium iodide were added to that medium and heated to 110° C. for 48 hours. It was poured into water, extracted with dichloromethane, washed with a solution of sodium bicarbonate, dried over sodium sulphate and concentrated to dryness. It was then purified by flash chromatography over silica (eluent: methanol-methylene chloride, 10/90). In this manner, 2.9 g of the desired compound was obtained. Yield: 65%.

c) (2-ethylindolizin-3-yl){4-[3-(diethylamino)propyl]phenyl}methanone oxalate 2.9 g of the product described above was dissolved in 40 ml of ethyl acetate and 0.719 g (1 equivalent) of oxalic acid was added. Next, the salt which crystallized out was filtered. In this manner, 2.9 g of the desired compound was obtained.
Yield: 80% MP=160° C.
$^1$H NMR spectrum (200 MHz, (DMSO), δ in ppm); 0.98 (t: 3H); 1.15 (t: 6H); 1.96 (m: 2H); 2.20 (q: 2H); 2.74 (t: 2H); 2.90-3.19 (m: 6H); 6.54 (s: 1H); 6.93 (t: 1H); 7.21 (t: 1H); 7.31-7.58 (AA'-BB' system: 4H); 7.64 (d: 1H); 9.47 (d: 1H); 8.39 (bs: 2H).

EXAMPLE 3

(2-butylindolizin-3-yl){4-[3-(dipropylamino)propyl]phenyl}methanone hydrochloride (compound 7)

a) 2-methyl-1-(2-oxo-hexyl)-pyridinium bromide 30.21 g of 2-picoline (0.32 mole) was slowly added to 83 g of 1-bromo-2-hexanone (0.46 mole) and stirred for 4 hours at ambient temperature. A viscous medium was obtained which was used as is for the next step.

b) 2-butylindolizine

The N-(hexanone-2-yl)methyl-pyridinium bromide obtained above was dissolved in 100 ml of ethanol and 84 g of sodium bicarbonate in solution in 630 ml of water was added. The reaction medium was heated for 3 h at 110° C. It was vacuum concentrated, taken up in water, extracted with dichloromethane, the organic phase was washed with a sodium chloride solution, dried over sodium sulphate and evaporated to dryness. The product obtained was purified on a silica column under pressure (eluent: methylene chloride/heptane, 20/80). In this manner, 33 g of 2-butylindolizine was obtained.
Yield: 30% c) 2-butylindolizin-3-yl)[4-(3-chloropropyl)phenyl]methanone

A mixture of 9 g (56 mmoles) of 2-butyl-indolizine and 12.4 g (57 mmoles) of 4-(3-chloropropyl)benzoyl chloride was heated to 50° C. for 18 hours. It was taken up in water, extracted with dichloromethane, washed with sodium carbonate solution, the organic phase was dried over sodium sulphate and concentrated to dryness. Next, it was purified by flash chromatography over silica (eluent: methylene chloride-heptane, 80/20). In this manner, 14 g of the desired compound was obtained in the form of an oil.
Yield: 77% d) (2-butylindolizin-3-yl){4-[3-(dipropylamino)propyl]phenyl}methanone 6 g (17 mmoles) of the compound obtained in the preceding step was dissolved in a reactor in 60 ml of methylisobutylketone and 4.4 g (44 mmoles) of dipropylamine and 0.5 g (3.4 mmoles) of sodium iodide were added, then the medium was heated to 110° C. for 48 hours. It was poured into water, extracted with dichloromethane, washed with a sodium bicarbonate solution, dried over sodium sulphate and concentrated to dryness.

It was then purified by flash chromatography over alumina (eluent: methylene chloride/methanol, 98/2).

In this manner, 6.2 g of the desired compound was obtained.
Yield: 88% e) (2-butylindolizin-3-yl){4-[3-(dipropylamino)propyl]phenyl}methanone hydrochloride 11 ml of a solution of hydrochloric ether (2M in ether) was added to a solution of the product described above (6.2 g) in ether (100 ml) and stirred for 30 minutes. It was vacuum concentrated, taken up in the ethyl acetate (60 ml) and the product which crystallized out was filtered. In this manner, 6.3 g of the desired compound was obtained.
Yield: 95% MP=115° C.
$^1$H NMR spectrum (200 MHz, (DMSO), δ in ppm); 0.64 (t: 3H); 0.78-1.12 (m: 8H); 1.33 (qui: 2H); 1.66 (mt: 4H); 2.02 (mt: 2H); 2.20 (t: 2H); 2.74 (t: 2H); 2.85-3.15 (m: 6H); 6.50 (s: 1H); 6.92 (t: 1H); 7.20 (t: 1H); 7.30-7.57 (AA'-BB' system: 4H); 7.62 (d: 1H), 9.45 (d: 1H); 10.60 (bs: 1H)

(2-Butylindolizin-3-yl){4-[3-(dipropylamino)propyl]phenyl}methanone hydrochloride hemihydrate 11 ml of water were added to a solution of (2-butylindolizin-3-yl){4-[3-(dipropylamino)propyl]phenyl}methanone (500 g) in ethyl acetate (796 ml). A solution of hydrochloric ether (2M in ether) was added to this coloured solution, cooled to 10° C. The medium was seeded and then maintained for three hours under isothermal conditions. The product obtained was filtered, washed with methyl isobutyl ketone and dried.

In this manner, 478.5 g of the desired compound was obtained.
Yield: 86.3%

The NMR analysis confirmed the structure of the compound.

DSC ("Differential Scanning Calorimetry"): Endotherm at 95.2° C. corresponding to the loss of water, followed by an endotherm at 117.1° C. corresponding to melting.

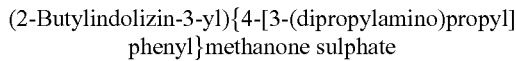
(2-Butylindolizin-3-yl){4-[3-(dipropylamino)propyl]phenyl}methanone sulphate A solution of sulfuric acid in ethyl acetate was added to a solution of (2-butylindolizin-3-yl){4-[3-(dipropylamino)propyl]phenyl}methanone (4.19 g) in ethyl acetate (30 ml) which have then been heated to 70° C. The medium was cooled to 20° C. and then, after an isothermal period at this temperature, the compound obtained was filtered, washed and dried.

In this manner, 4.4 g of the desired compound was obtained.

Yield: 85%

The NMR analysis confirmed the structure of the compound.

DSC: endotherm at 92° C. corresponding to melting.

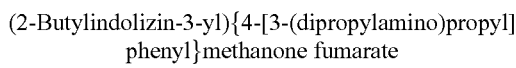
(2-Butylindolizin-3-yl){4-[3-(dipropylamino)propyl]phenyl}methanone fumarate A solution of fumaric acid in ethyl acetate was added to a solution of (2-butylindolizin-3-yl){4-[3-(dipropylamino)propyl]phenyl}methanone (9.5 g) in ethyl acetate (39 ml) which have then been heated to 50° C. The medium was cooled to 30° C., seeded, and then cooled to 5° C. After an isothermal period at this temperature, the compound obtained was filtered and dried. In this manner, 9.2 g of the desired compound were obtained.

Yield: 75.8%

The NMR analysis confirmed the structure of the compound.

DSC: melting endotherm at 83.9° C.

The following compounds were prepared using the methods described above in Examples 2 or 3, but using the appropriate starting products:

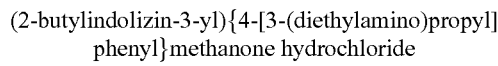
(2-butylindolizin-3-yl){4-[3-(diethylamino)propyl]phenyl}methanone hydrochloride

MP=145° C.

$^1$H NMR spectrum (200 MHz, (DMSO), δ in ppm); 0.65 (t: 3H); 0.99 (sxt: 2H); 1.18 (t: 6H); 1.34 (qui: 2H); 1.99 (mt: 2H); 2.20 (t: 2H); 2.75 (t: 2H); 2.93-3.22 (m: 6H); 6.50 (s: 1H); 6.92 (t: 1H); 7.20 (t: 1H); 7.32-7.57 (AA'-BB' system: 4H); 7.62 (d: 1H); 9.45 (d: 1H); 10.10 (bs: 1H)

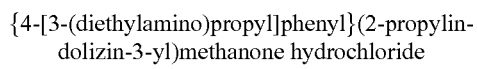
{4-[3-(diethylamino)propyl]phenyl}(2-propylindolizin-3-yl)methanone hydrochloride

MP=152° C.

$^1$H NMR spectrum (200 MHz, (DMSO), δ in ppm); 0.60 (t: 3H); 1.19- (t: 6H); 1.38 (sxt: 2H); 2.01 (mt: 2H); 2.17 (t: 2H); 2.75 (t: 2H); 2.89-3.21 (m: 6H); 6.51 (s: 1H); 6.92 (t: 1H); 7.20 (t: 1H); 7.32-7.57 (AA'-BB' system: 4H); 7.62 (d: 1H); 9.45 (d: 1H)-10.52 (bs: 1H)

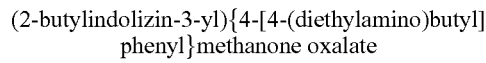
(2-butylindolizin-3-yl){4-[4-(diethylamino)butyl]phenyl}methanone oxalate

MP=102° C.

$^1$H NMR spectrum (200 MHz, (DMSO), δ in ppm); 0.64 (t: 3H); 0.98 (sxt: 2H); 1.17 (t: 6H); 1.33 (qui: 2H); 1.65 (t: 4H); 2.20 (t: 2H); 2.70 (t: 2H); 2.93-3.21 (m: 6H); 6.50 (s: 1H); 6.92 (t: 1H); 7.20 (t: 1H); 7.29-7.56 (AA'-BB' system: 4H); 7.62 (d: 1H), 9.45 (d: 1H)

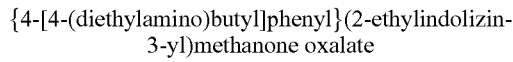
{4-[4-(diethylamino)butyl]phenyl}(2-ethylindolizin-3-yl)methanone oxalate

MP=143° C.

NMR spectrum $^1$H (200 MHz, (DMSO), δ in ppm); 0.98 (t: 3H); 1.15 (t: 6H); 1.64 mt: 4H); 2.20 (q: 2H); 2.72 (t: 2H); 2.89-3.19 (m: 6H); 6.53 (s: 1H); 6.92 (t: 1H); 7.20 (t: 1H); 7.29-7.57 (AA'-BB' system: 4H); 7.63 (d: 1H); 9.45 (d: 1H)

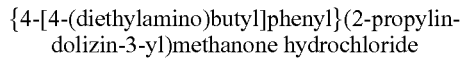
{4-[4-(diethylamino)butyl]phenyl}(2-propylindolizin-3-yl)methanone hydrochloride

MP=133° C.

$^1$H NMR spectrum (200 MHz, (DMSO), δ in ppm); 0.60 (t: 3H); 1.20 (t: 6H); 1.37 (sxt: 2H); 1.68 (mt: 4H); 2.17 (t: 2H); 2.71 (t: 2H); 2.90-3.18 (m: 6H); 6.50 (s: 1H); 6.93 (t: 1H); 7.20 (t: 1H); 7.29-7.57 (AA'-BB' system: 4H); 7.62 (d: 1H); 9.46 (d: 1H)-10.37 (bs: 1H)

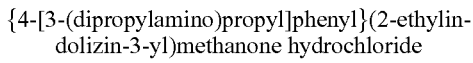
{4-[3-(dipropylamino)propyl]phenyl}(2-ethylindolizin-3-yl)methanone hydrochloride

MP=152° C.

$^1$H NMR spectrum (200 MHz, (DMSO), δ in ppm); 0.89 (t: 6H); 0.98 (t: 3H); 1.65 (mt: 4H); 2.03 (mt: 2H); 2.20 (q: 2H); 2.74 (t: 2H); 2.86-3.14 (m: 6H); 6.54 (s: 1H); 6.93 (t: 1H); 7.21 (t: 1H); 7.32-7.58 (AA'-BB' system: 4H); 7.63 (d: 1H); 9.47 (d: 1H); 10.46 (bs: 1H)

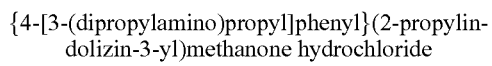
{4-[3-(dipropylamino)propyl]phenyl}(2-propylindolizin-3-yl)methanone hydrochloride

MP=122.6° C.

$^1$H NMR spectrum (200 MHz, (DMSO), δ in ppm); 0.60 (t: 3H); 0.89- (t: 6H); 1.3 (sx: 2H); 1.65 (m: 4H); 1.89-2.26 (m: 4H); 2.75 (t: 2H); 2.85-3.14 (m: 6H); 6.50 (s: 1H); 6.92 (t: 1H); 7.20 (t: 1H); 7.32-7.57 (AA-BB system: 4H); 7.62 (d: 1H); 9.45 (d: 1H)-10.47 (broad singlet: 1H)

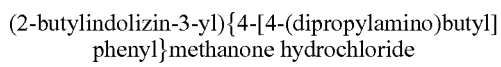
(2-butylindolizin-3-yl){4-[4-(dipropylamino)butyl]phenyl}methanone hydrochloride

MP=117° C.

$^1$H NMR spectrum (250 MHz, (DMSO), δ in ppm); 0.64 (t: 3H); 0.79-1.08 (superimposed multiplets: 8H); 1.31 (qui: 2H); 1.48-1.89 (superimposed multiplets: 8H); 2.18 (mt: 2H); 2.70 (mt: 2H); 2.78-3.17 (superimposed multiplets: 6H); 6.48 (s: 1H); 6.92 (t: 1H); 7.21 (t: 1H); 7.35 (d: 2H); 7.48 (d: 2H); 7.60 (d: 1H); 9.45 (d: 1H); 10.56 (broad signal: 1H)

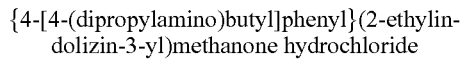
{4-[4-(dipropylamino)butyl]phenyl}(2-ethylindolizin-3-yl)methanone hydrochloride

MP=130° C.

$^1$H NMR spectrum (200 MHz, (DMSO), δ in ppm); 0.89 (t: 6H); 0.98 (t: 3H); 1.67 (mt: 8H); 2.21 (q: 2H); 2.71 (t: 2H);

2.81-3.19 (m: 6H); 6.53 (s: 1H); 6.93 (t: 1H); 7.20 (t: 1H); 7.29-7.57 (AA'-BB' system: 4H); 7.63 (d: 1H); 9.45 (d: 1H); 10.32 (bs: 1H)

4-[3-(dipropylamino)propyl]phenyl}(2-isopropylindolizin-3-yl)methanone hydrochloride MP=154° C.
$^1$H NMR spectrum (200 MHz, (DMSO-D$_6$), δ in ppm); 0.89 (t: 6H); 1.03 (d 6H); 1.64 (mt: 4H); 2.03 (mt: 2H); 2.54 (mt: 1H); 2.75 (t: 2H); 2.84-3.17 (m: 6H); 6.58 (s: 1H); 6.89 (t: 1H); 7.17 (t: 1H); 7.39 (d: 2H); 7.55 (d 2H); 7.62 (d: 1H); 9.32 (d: 1H); 10.54 (s: 1H)

{4-[3-(dipropylamino)propyl]phenyl}(2-methylindolizin-3-yl)methanone hydrochloride MP=146° C.
$^1$H NMR spectrum (200 MHz, (DMSO-D$_6$), δ in ppm); 0.87 (t: 6H); 1.62 (mt: 4H); 1.83 (s: 3H); 2.01 (mt: 2H); 2.17 (t: 2H); 2.84-3.12 (m: 6H); 6.46 (s: 1H); 6.94 (t: 1H); 7.22 (t: 1H); 7.38 (d: 2H); 7.49 (d: 2H); 7.61 (d: 1H); 9.55 (d: 1H); 10.42 (s: 1H)

{4-[4-(dipropylamino)butyl]phenyl}(2-isopropylindolizin-3-yl)methanone oxalate

MP=64° C.
$^1$H NMR spectrum (200 MHz, (DMSO-D$_6$), δ in ppm); 0.86 (t: 6H); 1.00 (d: 6H); 1.40-1.78 (m: 8H); 2.53 (mt: 1H); 2.69 (t: 2H); 2.81-3.15 (m: 6H); 6.58 (s: 1H); 6.87 (t: 1H); 7.16 (t: 1H); 7.34 (d: 2H); 7.54 (d: 2H); 7.60 (d: 1H); 9.30 (d: 1H)

{4-[4-(dipropylamino)butyl]phenyl}(2-methylindolizin-3-yl)methanone hydrochloride MP=141.1° C.
NMR spectrum $^1$H (200 MHz, (DMSO-D$_6$), δ in ppm); 0.89 (t: 6H); 1.48-1.79 (m: 8H); 1.85 (s: 3H); 2.71 (t: 2H); 2.82-3.18 (m: 6H); 6.46 (s: 1H); 6.95 (t: 1H); 7.22 (t: 1H); 7.35 (d: 2H); 7.48 (d: 2H); 7.62 (d: 1H); 9.54 (d: 1H); 10.26 (s: 1H)

(2-butylindolizin-3-yl){4-[3-(dibutylamino)propyl] phenyl}methanone hydrochloride MP=83° C.
$^1$H NMR spectrum (200 MHz, (DMSO), δ in ppm); 0.65 (t: 3H); 0.80-1.11 (m: 8H); 1.17-1.73 (m: 10H); 2.01 (mt: 2H); 2.20 (t: 2H); 2.74 (t: 2H); 2.90-3.16 (m: 6H); 6.50 (s: 1H); 6.92 (t: 1H); 7.20 (t: 1H); 7.32-7.57 (AA'BB' system: 4H); 7.62 (d: 1H); 9.45 (d: 1H); 10.25 (bs: 1H)

{4-[3-(dibutylamino)propyl]phenyl}(2-ethylindolizin-3-yl)methanone hydrochloride MP=94.5° C.
$^1$H NMR spectrum (200 MHz, (DMSO), δ in ppm); 0.90 (t: 6H); 0.99 (t: 3H); 1.30 (sxt: 4H); 1.61 (mt: 4H); 2.02 (mt: 2H); 2.21 (q: 2H); 2.75 (t: 2H); 2.87-3.18 (m: 6H); 6.55 (s: 1H); 6.94 (t: 1H); 7.22 (t: 1H)-7.31-7.59 (AA'-BB' system: 4H); 7.64 (d: 1H); 9.45 (d: 1H); 10.48 (bs: 1H)

{4-[3-(dibutylamino)propyl]phenyl}(2-propylindolizin-3-yl)methanone hydrochloride MP=120.6° C.
$^1$H NMR spectrum (200 MHz, (DMSO), δ in ppm); 0.60 (t: 3H); 0.89 (t: 6H); 1.13-1.75 (m: 10H); 1.87-1.25 (m: 4H); 2.74 (t: 2H); 2.88-3.15 (m: 6H); 6.50 (s: 1H); 6.93 (t: 1H); 7.20 (t: 1H); 7.31-7.57 (AA'-BB' system: 4H); 7.62 (d: 1H); 9.45 (d: 1H); 10.44 (bs: 1H)

(2-butylindolizin-3-yl){4-[4-(dibutylamino)butyl] phenyl}methanone oxalate

MP=101° C.
$^1$H NMR spectrum (200 MHz, (DMSO), δ in ppm); 0.64 (t: 3H); 0.79-1.14 (superimposed multiplets: 8H); 1.14-1.45 (multiple superimposed multiplets: 6H); 1.45-1.85 (multiple superimposed multiplets: 8H); 2.20 (mt: 2H); 2.70 (mt: 2H); 2.87-3.20 (superimposed multiplets: 6H); 6.50 (s: 1H); 6.92 (t: 1H); 7.18 (t: 1H); 7.34 (d: 2H); 7.49 (d: 2H); 7.61 (d: 1H); 9.44 (d: 1H)

{4-[4-(dibutylamino)butyl]phenyl}(2-ethylindolizin-3-yl)methanone oxalate

MP=96-101° C.
$^1$H NMR spectrum (200 MHz, (DMSO), δ in ppm); 0.89 (t: 6H); 0.98 (t: 3H); 1.30 (sxt: 4H); 1.43-1.79 (m: 8H); 2.21 (q: 2H); 2.72 (t: 2H); 2.82-3.14 (m: 6H); 6.53 (s: 1H); 6.92 (t: 1H); 7.20 (t: 1H); 7.29-7.57 (AA'-BB' system: 4H); 7.63 (d: 1H); 9.45 (d: 1H)

{4-[4-(dibutylamino)butyl]phenyl}(2-propylindolizin-3-yl)methanone oxalate

MP=154.6° C.
$^1$H NMR spectrum (200 MHz, (DMSO), δ in ppm); 0.60 (t: 3H); 0.90 (t: 6H); 1.12-1.82 (m: 14H); 2.17 (t: 2H); 2.71 (t: 2H) 2.84-3.18 (m: 6H); 6.50 (s: 1H); 6.93 (t: 1H); 7.20 (t: 1H); 7.29-7.57 (AA'-BB' system: 4H); 7.62 (d: 1H)-9.45 (d: 1H)

(2-butylindolizin-3-yl)(4-{3-[ethyl(propyl)amino] propyl}phenyl)methanone hydrochloride MP=120° C.
$^1$H NMR spectrum (200 MHz, (DMSO), δ in ppm); 0.65 (t: 3H); 0.81-1.10 (m: 5H); 1.11-1.45 (m: 5H); 1.65 (mt: 2H); 2.01 (mt: 2H); 2.20 (t: 2H); 2.74 (t: 2H); 2.86-3.21 (m: 6H); 6.50 (s: 1H); 6.92 (t: 1H); 7.20 (t: 1H); 7.31-7.57 (AA'-BB' system: 4H); 7.62 (d: 1H), 9.45 (d: 1H); 10.53 (bs: 1H)

(2-ethylindolizin-3-yl)(4-{3-[ethyl(propyl)amino] propyl}phenyl)methanone oxalate MP=160° C.
$^1$H NMR spectrum (200 MHz, (DMSO), δ in ppm); 0.89 (t: 3H); 0.98 (t: 3H); 1.15 (t: 3H); 1.56 (mt: 2H); 1.97 (mt: 2H); 2.20 (q: 2H); 2.73 (t: 2H); 2.86-3.19 (m: 6H); 6.54 (s: 1H); 6.93 (t: 4H); 7.21 (t: 1H); 7.30-7.58 (AA'-BB' system: 4H); 7.63 (d: 1H) 9.47 (d: 1H); 5.40-7.31 (bs: 2H)

(4-{3-[ethyl(propyl)amino]propyl}phenyl)(2-isopropylindolizin-3-yl)methanone hydrochloride MP=130° C.
$^1$H NMR spectrum (200 MHz, (DMSO-D$_6$), δ in ppm); 0.87 (t: 3H); 1.00 (d: 6H); 1.16 (t: 3H); 1.62 (mt: 2H); 2.00

(mt: 2H); 2.53 (mt: 1H); 2.73 (t: 2H); 2.84-3.17 (m: 6H); 6.57 (s: 1H); 6.88 (t: 1H); 7.16 (t: 1H); 7.38 (d: 2H); 7.55 (d: 2H); 7.61 (d: 1H); 9.32 (d: 1H); 10.48 (s: 1H)

(4-{3-[ethyl(propyl)amino]propyl}phenyl)(2-methylindolizin-3-yl)methanone hydrochloride

MP=147.9° C.

$^1$H NMR spectrum (200 MHz, (DMSO), δ in ppm); 0.89 (t: 3H); 0.98 (t: 3H); 1.15 (t: 3H); 1.56 (m: 2H); 1.97 (m: 2H); 2.20 (q: 2H); 2.73 (t: 2H); 2.86-3.19 (m: 6H); 6.54 (s: 1H); 6.93 (t: 4H); 7.21 (t: 1H); 7.30-7.58 (AA'-BB' system: 4H); 7.63 (d: 1H) 9.47 (d: 1H); 5.40-7.31 (broad signal: 2H)

(4-{4-[ethyl(propyl)amino]butyl}phenyl)(2-isopropylindolizin-3-yl)methanone oxalate

MP=136° C.

$^1$H NMR spectrum (200 MHz, (DMSO-D$_6$), δ in ppm); 0.89 (t: 3H); 1.03 (d: 6H); 1.17 (t: 3H); 1.47-1.80 (m: 6H); 2.55 (mt: 1H); 2.72 (t: 2H); 2.84-3.19 (m: 6H); 6.58 (s: 1H); 6.88 (t: 1H); 7.17 (t: 1H); 7.35 (d: 2H); 7.54 (d: 2H); 7.62 (d: 1H); 9.31 (d: 1H); 5.50-8.00 (bs: 2H)

(4-{4-[ethyl(propyl)amino]butyl}phenyl)(2-methylindolizin-3-yl)methanone hydrochloride

MP=141.1° C.

$^1$H NMR spectrum (200 MHz, (DMSO-D$_6$), δ in ppm); 0.89 (t: 3H); 1.20 (t: 3H); 1.43-1.79 (m: 6H); 1.86 (s: 3H); 2.71 (t: 2H); 2.82-3.22 (m: 6H); 6.46 (s: 1H); 6.95 (t: 1H); 7.22 (t: 1H); 7.35 (d: 2H); 7.48 (d: 2H); 7.62 (d: 1H); 9.55 (d: 1H); 10.30 (s: 1H)

(4-{3-[ethyl(propyl)amino]propyl}phenyl)(2-propylindolizin-3-yl)methanone hydrochloride

MP=108.7° C.

$^1$H NMR spectrum (200 MHz, (DMSO), δ in ppm); 0.60 (t: 3H); 0.89- (t: 3H); 1.19 (t: 3H); 1.38 (sxt: 2H); 1.64 (mt: 2H); 1.89-2.26 (m: 4H); 2.75 (t: 2H); 2.85-3.21 (m: 6H); 6.51 (s: 1H); 6.93 (t: 1H); 7.20 (t: 4H); 7.31-7.58 (AA'-BB' system: 4H); 7.62 (d: 1H)-9.45 (d: 1H)-10.38 (bs: 1H)

(2-butylindolizin-3-yl)(4-{4-[ethyl(propyl)amino]butyl}phenyl)methanone hydrochloride

MP=125° C.

$^1$H NMR spectrum (200 MHz, (DMSO), δ in ppm); 0.63 (t: 3H); 0.77-1.10 (m: 5H); 1.11-1.45 (m: 5H); 1.67 (mt: 6H); 2.19 (t: 2H); 2.70 (t: 2H); 2.82-3.21 (m: 6H); 6.50 (s: 1H); 6.91 (t: 1H); 7.19 (t: 1H); 7.29-7.55 (AA'-BB' system: 4H); 7.61 (d: 1H); 9.45 (d: 1H)-10.55 (bs: 1H)

(2-ethylindolizin-3-yl)(4-{4-[ethyl(propyl)amino]butyl}phenyl)methanone oxalate

MP=132° C.

$^1$H NMR spectrum (200 MHz, (DMSO), δ in ppm); 0.72-1.35 (m: 9H); 1.65- (bs: 6H); 2.20 (q: 2H); 2.70 (bs: 2H); 2.82-3.21 (m: 6H); 6.54 (s: 1H); 6.93 (t: 1H); 7.20 (t: 1H); 7.27-7.57 (AA'-BB' system: 4H); 7.63 (d: 1H); 7.63 (d: 1H); 9.45 (d: 1H); 8.20-10 (bs: 1H)

(4-{4-[ethyl(propyl)amino]butyl}phenyl)(2-propylindolizin-3-yl)methanone hydrochloride

MP=133° C.

$^1$H NMR spectrum (200 MHz, (DMSO), δ in ppm); 0.57 (t: 3H); 0.87 (t: 3H); 1.18 (t: 3H); 1.35 (sxt: 2H); 1.65 (m: 6H); 2.14 (t: 2H); 2.69 (t: 2H); 2.80-3.18 (m: 6H); 6.49 (s: 1H); 6.91 (t: 1H); 7.19 (t: 1H); 7.27-7.56 (AA'-BB' system: 4H); 7.61 (d: 1H); 9.45 (d: 1H); 10.28 (bs: 1H)

(2-butylindolizin-3-yl)(4-{3-[butyl(propyl)amino]propyl}phenyl)methanone oxalate

MP=142° C.

$^1$H NMR spectrum (200 MHz, (DMSO), δ in ppm); 0.64 (t: 3H); 0.79-1.13 (superimposed multiplets: 8H); 1.14-1.45 (superimposed multiplets: 4H); 1.45-1.75 (superimposed multiplets: 4H); 1.96 (mt: 2H); 2.20 (mt: 2H); 2.73 (mt: 2H); 2.86-3.17 (superimposed multiplets: 6H); 6.51 (s: 1H); 6.92 (t: 1H); 7.20 (t: 1H); 7.38 (d: 2H); 7.52 (d: 2H); 7.62 (d: 1H); 9.46 (d: 1H)

(4-{3-[butyl(ethyl)amino]propyl}phenyl)(2-butylindolizin-3-yl)methanone oxalate

MP=112° C.

$^1$H NMR spectrum (200 MHz, (DMSO), δ in ppm); 0.64 (t: 3H); 0.79-1.08 (superimposed multiplets: 5H); 1.15 (t: 3H); 1.23-1.44 (superimposed multiplets: 4H); 1.55 (mt: 2H); 1.97 (mt: 2H); 2.20 (mt: 2H); 2.74 (t: 2H); 2.90-3.20 (superimposed multiplets: 6H); 6.51 (s: 1H); 6.92 (t: 1H); 7.21 (t: 1H); 7.39 (d: 2H); 7.52 (d: 2H); 7.62 (d: 1H); 9.46 (d: 1H)

(2-butylindolizin-3-yl)(4-{3-[(cyclopropylmethyl)(propyl)amino]propyl}phenyl)methanone hydrochloride

MP=101° C.

$^1$H NMR spectrum (200 MHz, (DMSO), δ in ppm); 0.34 (mt: 2H); 0.50-0.80 (superimposed multiplets: 5H); 0.80-1.17 (superimposed multiplets: 6H); 1.33 (qui: 2H); 1.63 (mt: 2H); 2.00 (mt: 2H); 2.20 (mt: 2H); 2.73 (t: 2H); 2.86-3.40 (superimposed multiplets: 6H); 6.51 (s: 1H); 6.95 (t: 1H); 7.19 (t: 1H); 7.38 (d: 2H); 7.52 (d: 2H); 7.60 (d: 1H); 9.45 (d: 1H)

{4-[4-(propylamino)butyl]phenyl}(2-propylindolizin-3-yl)methanone hydrochloride

MP=135.3° C.

$^1$H NMR spectrum (200 MHz, (DMSO-D$_6$), δ in ppm); 0.59 (t: 3H); 0.90 (t: 3H); 1.37 (sxt: 2H); 1.50-1.80 (m: 6H); 2.16 (t: 2H); 2.57-3.04 (m: 6H); 6.50 (s: 1H); 6.92 (t: 1H); 7.20 (t: 1H); 7.35 (d: 2H); 7.50 (d: 2H); 7.62 (d: 1H); 8.92 (s: 2H); 9.45 (d: 1H)

(2-butylindolizin-3-yl){4-[3-(propylamino)propyl]phenyl}methanone hydrochloride

MP=178.2° C.

$^1$H NMR spectrum (200 MHz, (DMSO-D$_6$), δ in ppm); 0.62 (t: 3H); 0.78-1.07 (m: 5H); 1.31 (qui: 2H); 1.62 (sxt: 2H); 1.96 (qui: 2H); 2.17 (t: 2H); 2.61-2.99 (m: 6H); 6.49 (s: 1H); 6.91 (t: 1H); 7.20 (t: 1H); 7.36 (d: 2H); 7.51 (d: 2H); 7.61 (d: 1H); 8.99 (s: 2H); 9.46 (d: 1H)

(2-butylindolizin-3-yl){4-[3-(dimethylamino)propyl]phenyl}methanone hydrochloride MP=133.6° C.
¹H NMR spectrum (200 MHz, (DMSO-$D_6$), δ in ppm); 0.64 (t: 3H); 0.99 (sxt: 2H); 1.34 (qui: 2H); 2.02 (m: 2H); 2.20 (t: 2H); 2.59-2.87 (m: 8H); 3.04 (m: 2H); 6.50 (s: 1H); 6.92 (t: 1H); 7.20 (t: 1H); 7.37 (d: 2H); 7.51 (d: 2H); 7.62 (d: 1H); 9.46 (d: 1H); 10.78 (s: 1H)

(2-butylindolizin-3-yl)(4-{3-[(3R,5S)-3,5-dimethylpiperazin-1-yl]propyl}phenyl)methanone hydrochloride MH+=432.3
¹H NMR spectrum (200 MHz, (DMSO), δ in ppm); 0.65 (t: 3H); 0.98 (mt: 2H); 1.17-1.48 (superimposed multiplets: 8H); 1.93-2.32 (superimposed multiplets: 4H); 2.75 (t: 2H); 3.13 (mt: 4H); 3.73 (mt: 4H); 6.51 (s: 1H); 6.92 (t: 1H); 7.21 (t: 1H); 7.39 (d: 2H); 7.53 (d: 2H); 7.63 (d: 1H); 9.45 (d: 1H); 9.96 (broad signal: 2H); 12.06 (broad signal: 1H)

(2-butylindolizin-3-yl)(4-{3-[(3R,5S)-3,4,5-trimethylpiperazin-1-yl]propyl}phenyl)methanone hydrochloride MP=191-201° C.
¹H NMR spectrum (200 MHz, (DMSO), δ in ppm); 0.65 (t: 3H); 0.98 (mt: 2H); 1.15-1.58 (superimposed multiplets: 8H); 1.93-2.38 (superimposed multiplets: 4H); 2.50-2.90 (superimposed multiplets: 5H); 2.95-4.50 (superimposed multiplets: 8H); 6.55 (s: 1H); 6.92 (t: 1H); 7.21 (t: 1H); 7.39 (d: 2H); 7.53 (d: 2H); 7.63 (d: 1H); 9.45 (d: 1H); 11.95 (broad signal: 2H)

(4-{3-[bis(2-methoxyethyl)amino]propyl}phenyl)(2-butylindolizin-3-yl)methanone oxalate MP=137-139° C.
¹H NMR spectrum (200 MHz, (DMSO), δ in ppm); 0.65 (t: 3H); 0.98 (mt: 2H); 1.33 (mt: 2H); 1.90 (mt: 2H); 2.19 (mt: 2H); 2.69 (mt: 2H); 2.95 (mt: 2H); 3.12 (mt: 4H); 3.26 (s: 6H); 3.55 (mt: 4H); 6.51 (s: 1H); 6.92 (t: 1H); 7.20 (t: 1H); 7.34 (d: 2H); 7.51 (d: 2H); 7.63 (d: 1H); 9.46 (d: 1H).

(2-butylindolizin-3-yl)[4-(3-piperidin-1-ylpropyl)phenyl]methanone oxalate

MP=191-192° C.
¹H NMR spectrum (200 MHz, (DMSO), δ in ppm); 0.65 (t: 3H); 0.98 (mt: 2H); 1.33 (mt: 2H); 1.53 (mt: 2H); 1.71 (superimposed multiplets: 4H); 2.00 (mt: 2H); 2.20 (mt: 2H); 2.70 (t: 2H); 2.88-3.30 (superimposed multiplets: 6H); 6.52 (s: 1H); 6.92 (t: 1H); 7.28 (t: 1H); 7.37 (d: 2H); 7.52 (d: 2H); 7.63 (d: 1H); 9.45 (d: 1H).

EXAMPLE 4

{4-[4-(dipropylamino)butyl]phenyl}(2-propylindolizin-3-yl)methanone hydrochloride (compound 16)

a) (2-propylindolizin-3-yl)[4-(4-chlorobutyl)phenyl]methanone

A mixture of 11 g (69 mmoles) of 2-propyl indolizine and 15.9 g (69 mmoles) of 4-(4-chlorobutyl)benzoyl chloride was heated to 50° C. for 18 hours. It was taken up in water, extracted with dichloromethane, washed with a sodium carbonate solution, the organic phase was dried over sodium sulphate and concentrated to dryness. It was purified by flash chromatography over alumina (eluent: heptane/methylene chloride, 50/50).

In this manner, 23 g of the desired compound was obtained in the form of an oil.
Yield: 94.2% b) (2-propylindolizin-3-yl)-{4-[4-(dipropylamino)butyl]phenyl}methanone 4 g (11.3 mmoles) of the compound obtained in the preceding step was dissolved in a reactor in 50 ml of methyl isobutylketone and 2.9 g (29.3 mmoles) of dipropylamine and 0.33 g (2 26 mmoles) of sodium iodide were added to this reaction medium and heated to 110° C. for 72 hours.

It was poured into water, extracted with dichloromethane, washed with a sodium bicarbonate solution and concentrated to dryness. It was then purified by flash chromatography on silica (eluent: methylene chloride/methanol, 95/5).

In this manner, 3.9 g of the desired compound was obtained.
Yield: 82.9% c) (2-propylindolizin-3-yl)-{4-[4-(dipropylamino)butyl]phenyl}methanone hydrochloride 7 ml of a solution of hydrochloric ether (2M in ether) was added to a solution of the product described above, 3.9 g in ether (50 ml), stirred for 30 minutes and the salt which crystallized out was filtered.

In this manner, 3.1 g of the desired compound was obtained.
Yield: 73%
MP=93° C.
¹H NMR spectrum (200 MHz, (DMSO), δ in ppm); 0.60 (t: 3H); 0.90 (t: 6H); 1.38 (sxt: 2H); 1.52-1.85 (m: 8H); 2.17 (t: 2H) 2.71 (t: 2H); 2.84-3.18 (m: 6H); 6.50 (s: 1H); 6.93 (t: 1H); 7.20 (t: 1H); 7.29-7.57 (AA'-BB' system: 4H); 7.62 (d: 1H); 9.45 (d: 1H)-10.23 (bs: 1H)

The solubility tests were carried out at pH=4 as follows:

A phosphate buffer, pH6, 0.1M, was prepared by adding 6.15 ml of 0.1M $Na_2HPO_4$ to 43.85 ml of 0.1M $NaH_2PO_4$. The solution was made up to 100 ml with filtered water using a Millipore system (trade mark).

Reference (Test Product in a Concentration in which the Latter is Soluble and which Acts as an Internal Reference)

About 0.2 mg (in a boat) was weighed out exactly and diluted in 1 ml of $H_2O/CH_3CN$: (50:50), i.e. 0.2 mg/ml, then the sample was subjected to ultrasound for 5 minutes.

Test Product Sample:

About 4 mg (in a boat) was weighed out exactly and diluted in 400 μl (i.e. 10 mg/ml) of pH6 phosphate buffer (0.1M), then the sample was subjected to ultrasound for 5 minutes.

The pH was noted and if the pH was below 4, 1 μl of NaOH 1N was added (from 1 μl in 1 μl) until the pH was more than 4, then the pH was noted again. The solution (0.45 μm) was filtered then if necessary diluted with the phosphate buffer pH6. (If the product re-precipitated after diluting, the diluted sample was ignored, the mother solution was used and the solubility was determined at a wavelength other than λmax, to avoid saturating the signal.

The solubility of the compound was then determined by HPLC under the following conditions:

Experimental Conditions

Instrument: Agilent 1100 chromatograph

Software: Chemstation

Column: XTERRA C18 (150×4.6 mm; 3.5 μm)

Eluent A: $H_2O/CH_3CN/CH_3SO_3H$: 1000/25/1

Eluent B: $H_2O/CH_3CN/CH_3SO_3H$: 25/1000/1

Gradient:

| Time (min) | A | B |
|---|---|---|
| 0 | 90 | 10 |
| 8 | 0 | 100 |
| 16 | 0 | 100 |
| 17-20 | 90 | 10 |

Column temperature: 30° C.

Flow rate: 0.8 ml/min

Detection: λ=230 nm

Injection volume: 5 μl

What is claimed is:

1. A compound of the formula (I):

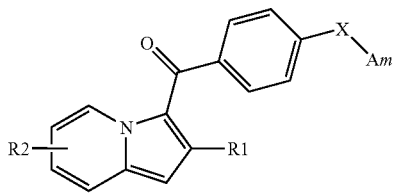

in which:
X represents a —$(CH_2)_n$— radical where n is a whole number from 1 to 6, or a group with formula $CH_2$—Z—$(CH_2)_2$—, in which Z represents an $O(CH_2)_m$— group in which m is a whole number from 0 to 3; $R_1$ represents a linear, branched or cyclic $C_1$-$C_8$ alkyl radical; Am represents an $NR_3R_4$ group in which $R_3$ and $R_4$ are identical or different and independently of each other represent:
a hydrogen atom;
a linear, branched or cyclic $C_1$-$C_6$ alkyl radical or a $C_1$-$C_3$ radical substituted with a $C_3$-$C_6$ cycloalkyl radical;
or a $(CH_2)_l$—O—B radical in which B represents a hydrogen atom or a $(CH_2)_kH$ alkyl radical, where l and k are whole numbers, $l \geqq 2$ and $l+k \leqq 6$;
or $R_3$ and $R_4$ together with the nitrogen atom to which they are attached form a heterocycle containing 4 to 6 links which may optionally contain one or more heteroatoms selected from N and O and optionally carrying one or more substituents selected from a linear, branched or cyclic $C_1$-$C_6$ alkyl radical;
$R_2$ represents a hydrogen atom or a linear, branched or cyclic $C_1$-$C_6$ alkyl radical;
and their pharmaceutically acceptable salts.

2. A compound according to claim 1, wherein X represents a —$(CH_2)_n$— radical where n is a whole number from 1 to 6.

3. A compound according to claim 1, wherein X represents a $(CH_2)_n$— radical where n is a whole number from 3 to 4.

4. A compound according to claim 1, wherein X represents a group with formula $CH_2$—Z—$(CH_2)_2$—, in which Z represents an $O(CH_2)_m$— group in which m is a whole number from 0 to 3.

5. Indolizine derivatives according to claim 1 wherein $R_1$ represents a $C_1$-$C_4$ alkyl radical.

6. A compound according to claim 1, wherein $R_3$ and $R_4$ independently of each other represent a linear $C_1$-$C_4$ alkyl radical.

7. A compound according to claim 1, wherein $R_3$ and $R_4$ together form a piperidinyl or piperazinyl group optionally carrying one or more methyl radicals.

8. A compound according to claim 1, wherein $R_2$ represents a hydrogen atom.

9. A compound according to claim 1, wherein the pharmaceutically acceptable salt is selected from an oxalate and a hydrochloride.

10. A compound of formula (I) selected from:
(2-butylindolizin-3-yl){4-[3-(diethylamino)propyl]phenyl}methanone hydrochloride;
(2-ethylindolizin-3-yl){4-[3-(diethylamino)propyl]phenyl}methanone oxalate;
{4-[3-(diethylamino)propyl]phenyl}(2-propylindolizin-3-yl)methanone hydrochloride;
(2-butylindolizin-3-yl){4-[4-(diethylamino)butyl]phenyl}methanone oxalate;
{4-[4-(diethylamino)butyl]phenyl}(2-ethylindolizin-3-yl)methanone oxalate;
{4-[4-(diethylamino)butyl]phenyl}(2-propylindolizin-3-yl)methanone hydrochloride;
(2-butylindolizin-3-yl){4-[3-(dipropylamino)propyl]phenyl}methanone hydrochloride;
(2-butylindolizin-3-yl){4-[3-(dipropylamino)propyl]phenyl}methanone hydrochloride hemihydrate;
(2-butylindolizin-3-yl){4-[3-(dipropylamino)propyl]phenyl}methanone sulphate;
(2-butylindolizin-3-yl){4-[3-(dipropylamino)propyl]phenyl}methanone fumarate;
{4-[3-(dipropylamino)propyl]phenyl}(2-ethyl indolizin-3-yl)methanone hydrochloride;
{4-[3-(dipropylamino)propyl]phenyl}(2-propylindolizin-3-yl)methanone hydrochloride;
(2-butylindolizin-3-yl){4-[4-(dipropylamino)butyl]phenyl}methanone hydrochloride;
{4-[4-(dipropylamino)butyl]phenyl}(2-ethylindolizin-3-yl)methanone hydrochloride;
4-[3-(dipropylamino)propyl]phenyl}(2-isopropylindolizin-3-yl)methanone hydrochloride;
{4-[3-(dipropylamino)propyl]phenyl}(2-methylindolizin-3-yl)methanone hydrochloride;
{4-[4-(dipropylamino)butyl]phenyl}(2-isopropylindolizin-3-yl)methanone oxalate;
{4-[4-(dipropylamino)butyl]phenyl}(2-methylindolizin-3-yl)methanone hydrochloride;
{4-[4-(dipropylamino)butyl]phenyl}(2-propylindolizin-3-yl)methanone hydrochloride;
(2-butylindolizin-3-yl){4-[3-(dibutylamino)propyl]phenyl}methanone hydrochloride;
Hydrochloride {4-[3-(dibutylamino)propyl]phenyl}(2-ethylindolizin-3-yl)methanone;
{4-[3-(dibutylamino)propyl]phenyl}(2-propylindolizin-3-yl)methanone hydrochloride;
(2-butylindolizin-3-yl){4-[4-(dibutylamino)butyl]phenyl}methanone oxalate;

{4-[4-(dibutylamino)butyl]phenyl}(2-ethylindolizin-3-yl)methanone oxalate;
{4-[4-(dibutylamino)butyl]phenyl}(2-propylindolizin-3-yl)methanone oxalate;
(2-butylindolizin-3-yl)(4-{3-[ethyl(propyl)amino]propyl}phenyl)methanone hydrochloride;
(2-ethylindolizin-3-yl)(4-{3-[ethyl(propyl)amino]propyl}phenyl)methanone oxalate;
(4-{3-[ethyl(propyl)amino]propyl}phenyl)(2-isopropylindolizin-3-yl)methanone hydrochloride;
(4-{3-[ethyl(propyl)amino]propyl}phenyl)(2-methylindolizin-3-yl)methanone hydrochloride;
(4-{4-[ethyl(propyl)amino]butyl}phenyl)(2-isopropylindolizin-3-yl)methanone oxalate;
(4-{4-[ethyl(propyl)amino]butyl}phenyl)(2-methylindolizin-3-yl)methanone hydrochloride;
(4-{3-[ethyl(propyl)amino]propyl}phenyl)(2-propylindolizin-3-yl)methanone hydrochloride;
(2-butylindolizin-3-yl)(4-{4-[ethyl(propyl)amino]butyl}phenyl)methanone hydrochloride;
(2-ethylindolizin-3-yl)(4-{4-[ethyl(propyl)amino]butyl}phenyl)methanone oxalate;
(4-{4-[ethyl(propyl)amino]butyl}phenyl)(2-propylindolizin-3-yl)methanone hydrochloride;
(2-butylindolizin-3-yl)(4-{3-[butyl(propyl)amino]propyl}phenyl)methanone oxalate;
(4-{3-[butyl(ethyl)amino]propyl}phenyl)(2-butylindolizin-3-yl)methanone oxalate;
(2-butylindolizin-3-yl)(4-{3-[(cyclopropylmethyl)(propyl)amino]propyl}phenyl)methanone hydrochloride;
{4-[4-(propylamino)butyl]phenyl}(2-propylindolizin-3-yl)methanone hydrochloride;
(2-butylindolizin-3-yl){4-[3-(propylamino)propyl]phenyl}methanone hydrochloride;
(2-butylindolizin-3-yl){4-[3-(dimethylamino)propyl]phenyl}methanone hydrochloride;
(2-butyl indolizin-3-yl)(4-{3-[(3R,5S)-3,5-dimethylpiperazin-1-yl]propyl}phenyl)methanone hydrochloride;
(2-butyl indolizin-3-yl)(4-{3-[(3R,5S)-3,4,5-trimethylpiperazin-1-yl]propyl}phenyl)methanone hydrochloride;
(4-{3-[bis(2-methoxyethyl)amino]propyl}phenyl)(2-butylindolizin-3-yl)methanone oxalate;
(2-butylindolizin-3-yl)[4-(3-piperidin-1-ylpropyl)phenyl]methanone oxalate;
(2-butyl-6-methylindolizin-3-yl){4-[3-(dipropylamino)propyl]phenyl}methanone hydrochloride;
(2-butyl-6-ethylindolizin-3-yl){4-[3-(dipropylamino)propyl]phenyl}methanone hydrochloride;
(2-butyl-6-methylindolizin-3-yl)(4-{3-[ethyl(propyl)amino]propyl}phenyl)methanone hydrochloride; and
(2-butyl-6-ethylindolizin-3-yl)(4-{3-[ethyl(propyl)amino]propyl}phenyl)methanone hydrochloride.

11. A method for preparing compounds of formula (I) according to claim 1, said method comprising the step of reacting an amine H—Am with a compound of formula (II):

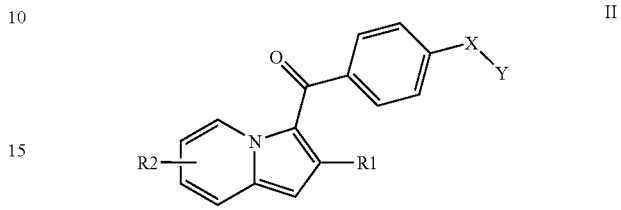

in which Y represents a halogen atom and the other substituents are as defined in claim 1.

12. A method for preparing a compound of formula (II) according to claim 11, said method comprising the step of reacting a compound of formula (III):

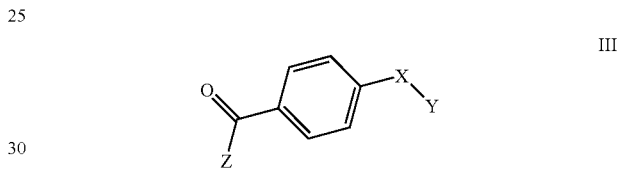

with a compound represented by formula (IV):

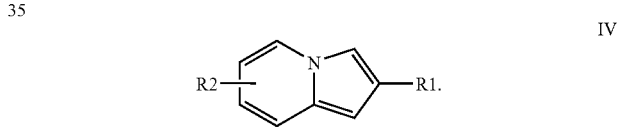

13. A compound of formula (I) according to claim 1, for use as a drug.

14. A composition comprising a compound of formula (I) of claim 1.

15. A pharmaceutical composition comprising, at least one compound of formula (I) according to claim 1, or a pharmaceutically acceptable salt thereof, in combination with a pharmaceutical vehicle or an appropriate excipient.

* * * * *